United States Patent [19]

Bartels et al.

[11] Patent Number: 4,621,632
[45] Date of Patent: Nov. 11, 1986

[54] HUMIDIFIER SYSTEM

[75] Inventors: Harold U. Bartels, Riverside; Finn Sveen, Redlands, both of Calif.

[73] Assignee: Bear Medical Systems, Inc., Riverside, Calif.

[21] Appl. No.: 667,142

[22] Filed: Nov. 1, 1984

[51] Int. Cl.$^4$ .......................................... A61M 16/00
[52] U.S. Cl. ......................... 128/203.27; 128/203.17; 261/130
[58] Field of Search ...................... 128/203.17, 203.27, 128/204.17, 200.14; 261/130, DIG. 65; 219/274

[56] References Cited

U.S. PATENT DOCUMENTS

| | | | |
|---|---|---|---|
| 3,282,266 | 11/1966 | Walker, Jr. | 128/209 |
| 3,434,471 | 3/1969 | Liston | 128/145.8 |
| 3,638,926 | 2/1972 | Melville et al. | 261/130 |
| 3,659,604 | 5/1972 | Melville et al. | 128/212 |
| 4,060,576 | 11/1977 | Grant et al. | 261/130 |
| 4,248,217 | 2/1981 | Brisson | 128/204.17 |
| 4,284,878 | 8/1981 | Bartels | 219/272 |
| 4,305,388 | 12/1981 | Brisson | 128/204.17 |
| 4,369,777 | 1/1983 | Lwoff et al. | 128/200.14 |
| 4,430,994 | 2/1984 | Clawson | 128/203.27 |
| 4,529,867 | 7/1985 | Velnosky et al. | 219/274 |

Primary Examiner—Kyle L. Howell
Assistant Examiner—Francis J. Jaworski
Attorney, Agent, or Firm—Klein & Szekeres

[57] ABSTRACT

A humidifier system including a humidifier chamber and heater assembly, microprocessor based control circuitry, and a housing for the control circuitry. The humidifier system is adapted to provide air at nearly 100 percent relative humidity and at a predetermined temperature (e.g. 35° C.) to a medical (e.g. critical care) patient. The humidifier chamber includes a continuous spiral heat exchange path which extends between a vapor storage chamber and an outlet of the humidifier chamber at which an air heating tube is connected, so that outgoing air can be delivered to the patient. The vapor storage chamber is interfaced with a ventilator source of incoming air and a relatively small reservoir in which a supply of water is boiled by the heater assembly for providing vapor saturated air from the vapor storage chamber to the heat exchange path. The control circuitry includes a pair of sensors which are responsive to the temperature of the outgoing humidified air at the humidifier chamber outlet and at the patient end of the heating tube. The temperatures sensed are used to control the energization of both the heater assembly and a heating element of the heating tube, so that humidified air can be delivered to the patient at the predetermined temperature and with minimal condensate rainout.

23 Claims, 9 Drawing Figures

HUMIDIFIER SYSTEM

BACKGROUND OF THE INVENTION

1. Field of the Invention

This invention relates to a compact, economical and efficient humidifier system for providing a supply of air at or near 100 percent relative humidity and a predetermined temperature to a medical (e.g. critical care) patient. The humidifier system is of the type which is adapted to be interfaced with an artificial respirator (i.e. ventilator) such as that commonly found in an intensive care unit of a medical facility.

2. Prior Art

Medical patients that are confined to an intensive care unit of a medical facility are commonly provided with a supply of breatheable air from an artificial respirator (i.e. ventilator) source. However, it is medically preferable to control the relative humidity and temperature of such air being delivered to the respiratory passages of the patient. More particularly, apparatus is desired which is capable of delivering, to a patient, air that is characterized by substantially 100 percent relative humidity and a temperature of 35° C. That is, breatheable air that is highly saturated with water vapor will minimize the drying out of the mucous membranes located in the patient's respiratory tract so as to lessen the chance of injury to delicate tissues and thereby reduce the possibility of an obstruction in the patient's breathing passage as a consequence of insufficient mucous flow. Moreover, it is advantageous to heat the patient's supply of breatheable air to a temperature which is at or near body temperature (e.g. 35° C.–37° C.), because vapor saturated air at body temperature contains more water vapor than vapor saturated air at room temperature (e.g. 20° C.–24° C.).

Accordingly, various humidifier devices are available to be interfaced with a ventilator for heating and humidifying a supply of air for delivery to a patient. However, such devices are typically characterized by one or more of the following shortcomings. By way of example, certain conventional devices, known as pot humidifiers, require a large reservoir supply of water (e.g. as much as 300 to 600 cc) to be heated for the purpose of generating water vapor. Due to the large thermal mass created by such a large reservoir supply, pot humidifiers are generally cumbersome and energy inefficient and usually require a relatively lengthy period of time from start-up before the reservoir water supply can be heated to a temperature suitable for producing vapor.

Moreover, in some pot humidifiers the characteristic large mass of water is overheated in order to produce vapor, with the heat of vaporization being used to compensate for heat losses in the delivery tubing which supplies humidified air to the patient. However, resulting condensate which is formed within the tubing must be drained at regular intervals. Such a humidifier system is inherently heavy and slow reacting. In addition, the system must be physically spaced from the patient to avoid excessive temperature fluctuations within the humidified air delivered to the patient. Humidifier systems which incorporate means to heat the tubing to overcome the foregoing are typically expensive and/or undesirably complex.

Other conventional humidifier devices, known as wick humidifiers, utilize an absorbent wick for the purpose of reducing the size of the reservoir water supply. However, and as will be known to those skilled in the art, such wicks have a relatively short lifespan and, therefor, require frequent replacement. In some cases, the wick is formed from blotting paper which is positioned in contact with a source of heat so as to permit the wick to rapidly reach operating temperature. However, such blotting paper is typically not reusable and both the cost of maintenance and time for reconditioning the wick humidifier are correspondingly increased.

Still other conventional humidifier devices lack the ability to precisely control the temperature of the air being delivered to the patient. Such devices do not include means to accurately sense the temperature of the air at both the humidifier outlet and patient ends of an air delivery (e.g. tubing) system. Thus, temperature variations which are frequently produced by changes in the air flow between the humidifier and the patient are often overlooked.

Reference may be made to one or more of the following United States patents for examples of a conventional humidifier system:

U.S. Pat. No. 3,282,266; Nov. 1, 1966
U.S. Pat. No. 3,434,471; Mar. 25, 1969
U.S. Pat. No. 3,638,926; Feb. 1, 1972
U.S. Pat. No. 3,659,604; May 2, 1972
U.S. Pat. No. 4,248,217; Feb. 3, 1981
U.S. Pat. No. 4,284,878; Aug. 18, 1981
U.S. Pat. No. 4,305,388; Dec. 15, 1981
U.S. Pat. No. 4,369,777; Jan. 25, 1983
U.S. Pat. No. 4,430,994; Feb. 14, 1984

By way of particular example, U.S. Pat. No. 3,434,471 discloses a humidifier for use with a ventilator. The humidifier includes a reservoir with a heat exchanger and heater. Air to be humidified is passed into the heat exchanger, whereupon it is heated. The heated air then passes above the water in the reservoir. Thus, the air becomes saturated with water vapor and is passed through a second heat exchanger, whereupon it is cooled to cause some moisture to "rain out" and thereby assure 100 percent relative humidity at the temperature at which the air exits the humidifier. The temperature of the air at the patient end is sensed by a thermistor which controls the output of the heater.

U.S. Pat. No. 3,638,926 discloses humidification and heating apparatus which comprises a spirally wound resistance-heated plate in thermal contact with a sheet of water absorbent blotting paper. Air from a respirator travels along a spiral passage formed by the plate, the water surface at a reservoir, and a lid to produce a substantially saturated vapor at a desired temperature.

U.S Pat. Nos. 4,248,217 and 4,305,388 generally relate to devices for controlling the heating of inspiratory gas as a function of the expiratory gas temperatures. Thermistors are used in each of the inspiratory and expiratory flow paths for sensing and controlling the heating of the gas.

SUMMARY OF THE INVENTION

Briefly, and in general terms, a compact, relatively low cost, and lightweight humidifier system is disclosed that avoids the shortcomings which characterize conventional humidifier systems. The present humidifier system is adapted to be interfaced with an artificial respirator (e.g. a ventilator) to deliver air at nearly 100 percent relative humidity and at a predetermined temperature to a patient, such as at an intensive care unit of a medical facility. The system includes a humidifier chamber and a heater assembly extending therewithin.

The humidifier chamber has a reservoir in which a relatively small supply of water is heated and boiled by the heater assembly. The heater assembly extends through the reservoir and contacts the water supply to quickly boil the water supply and thereby produce vapor. A vapor storage chamber is centrally disposed in the humidifier chamber and communicates with the reservoir for receiving a supply of vapor therefrom and with an inlet port for receiving a supply of incoming air from the ventilator, so that a supply of vapor saturated air is supplied at the vapor storage chamber. A continuous heat exchange surface spirals outwardly through the humidifier chamber from the centrally disposed vapor storage chamber to a peripherally disposed air outlet port. Thus, the vapor saturated air condenses as it traverses the heat exchange surface until heated air, at substantially 100 percent relative humidity, is provided at the air outlet port of the humidifier chamber. A tube extends between the air outlet port and the patient by which to deliver outgoing humidified air to the patient. The tube includes a heating element by which to heat the outgoing air to avoid condensation in the tube and minimize temperature fluctuations in the outgoing air being delivered to the patient.

The humidifier system also includes microprocessor based control circuitry having a pair of drivers for energizing the heater assembly and the heating element of the tube. First and second temperature sensors are responsive to the temperature of the outgoing humidified air at the humidifier chamber outlet port and the patient end of the tube, respectively. The temperatures sensed are compared with one another and with a predetermined temperature by a closed loop, dual servo controller for the purpose of regulating the duty cycle of and output power provided by the pair of drivers for controlling the energization of the heater assembly and the heating element of the tube. Therefore, the heat provided by the heater assembly and heating element of the tube can be adjusted, so that the outgoing humidified air can be delivered to the patient at the predetermined temperature and with minimum temperature fluctuation. The control circuitry also includes a plurality of indicator lamps located at a control panel of a housing, whereby the performance of the humidifier system can be monitored and visually displayed.

DESCRIPTION OF THE PREFERRED EMBODIMENT

Figure 1:
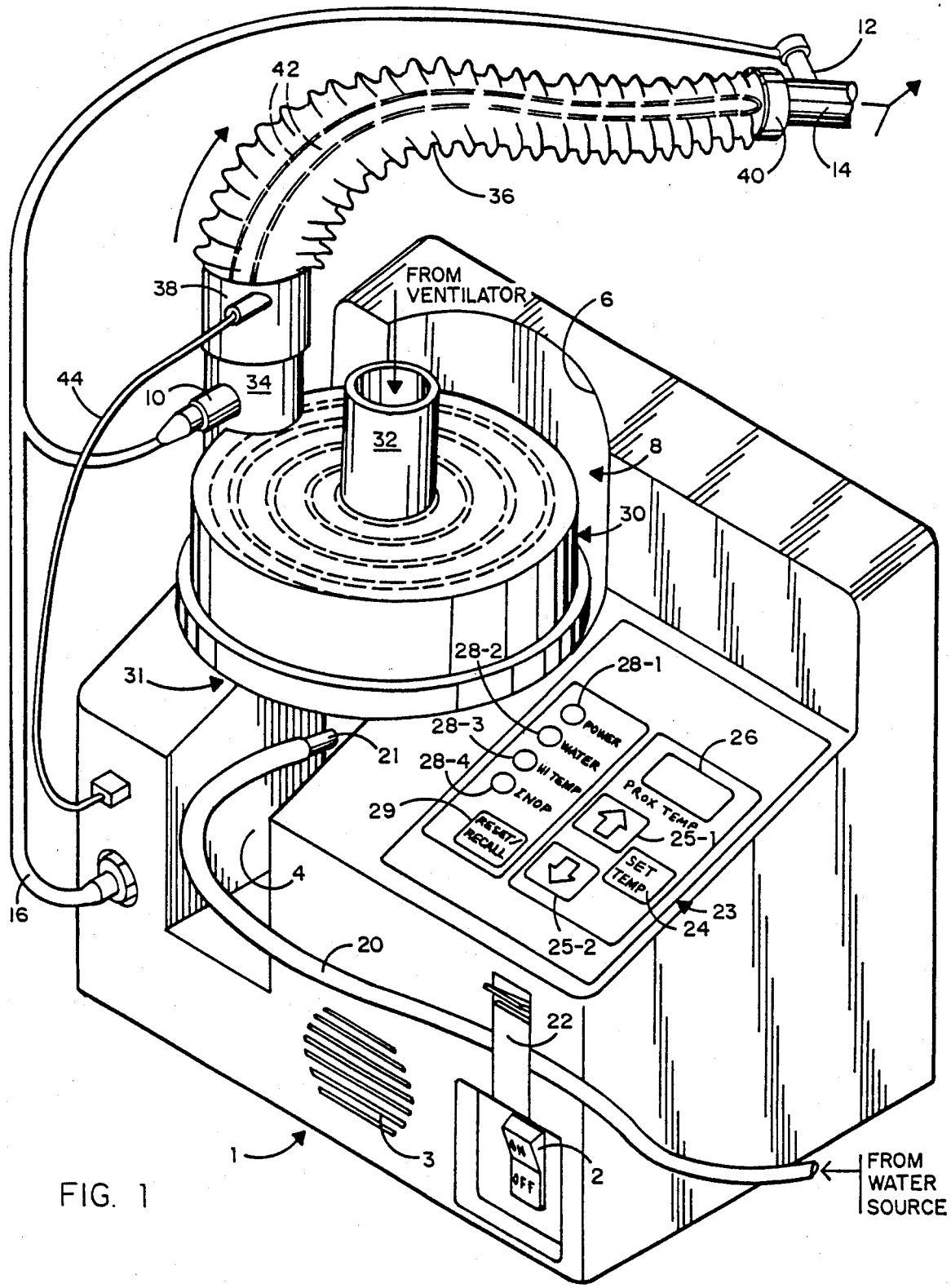
FIG. 1 is an isometric view illustrative of the housing and humidifier chamber which form part of the humidifier system of the present invention.

Referring now to the drawings, FIG. 1 illustrates the housing for the present humidifier system. Housing 1 includes a cavity 4 and recess 6 molded therein and adapted for the removable receipt of a humidifier chamber 8. The details of humidifier chamber 8 will be disclosed in greater detail hereinafter when referring to FIGS. 2-4 of the drawings. Briefly, however, chamber 4 comprises a cylindrical shroud portion 30 and a generally tapered base portion 31. Shroud portion 30 is located above the cavity 4 and within the recess 6 of housing 1. Base portion 31 (only a portion of which is shown in FIG. 1) extends from the interior of cavity 4 to a releasable connection with shroud portion 30.

Projecting upwardly from and coextensively formed with the cylindrical shroud portion 30 is a concentrically aligned air inlet port 32. In the assembled relationship, inlet port 32 is interfaced with a ventilator source, such as a mechanical lung, or the like, so as to receive a supply of incoming air by way of an air hose (not shown). Also projecting upwardly from and coextensively formed with shroud portion 30 is a peripherally disposed air outlet port 34. Outlet port 34 is shown interconnected with a flexible heating tube 36 at a coupling member 38. Heating tube 36 is preferably fabricated from silicone and is adapted to be sterilized (e.g. such as in an autoclave) so as to be reusable. Heating tube 36 has a length which is typically between four to six feet and terminates at a cuff 40 through which outgoing humidified air is supplied from outlet port 34 to the patient. Extending through heating tube 36 in a forward direction and then being bent backwards upon itself in a reverse direction is an optional heater element 42 (shown dotted). The heat provided by element 42 advantageously prevents the formation of condensation along the path of heating tube 36. Heater element 42 also compensates for temperature loss of the humidified air being conveyed between outlet port 34 and cuff 40. That is, heater element 42 generates heat which is equivalent to the heat dissipated along the heating tube 36 to the atmosphere, whereby to reduce temperature fluctuations and maintain the outgoing humidified air being delivered from humidifier chamber 8 to the patient at a substantially uniform temperature (e.g. 35° C.). In the event that heater element 42 is to be employed within heating tube 36, conventional electrical wiring 44 is interconnected between a source of current at housing 1 and heater element 42 at coupling 38. Wiring 44 provides electrical current by which to energize heater element 42 and thereby heat the outgoing humidified air which passes through heating tube 36 to the patient.

In accordance with the present invention, the temperature of the humidified air is controlled and maintained at a predetermined temperature (e.g. 35° C.) by sensing the air temperature as it exits the humidifier chamber 8 and as it is delivered to the patient (from the patient end of heating tube 36). Accordingly, an outlet temperature probe (e.g. a thermistor) 10 is associated with outlet port 34 to sense the temperature of the humidified air exiting humidifier chamber 8. Moreover, a proximal temperature probe (e.g. a thermistor) 12 is associated with cuff 40 to sense the proximal temperature of the humidified air being delivered to the patient from heating tube 36. More particularly, the cuff 40 is typically connected to a Y-shaped patient wye (only a portion of which is shown). One leg of the patient wye 14 supplies air to the respiratory system of the patient and (as illustrated) is in contact with temperature probe 12. The other leg (not shown) of coupling 14 is used to convey exhaust gases during the exhalation portion of the patient's breathing cycle. Each of the outlet and proximal temperature probes 10 and 12 is interconnected with control housing 1 via conventional wiring 16 for supplying temperature related information to the humidifier system control circuitry which, as will soon be described, is adapted to control the air temperature so that the patient is supplied with humidified air at a particular, predetermined temperature (e.g. 35° C.).

A delivery tube 20 is connected between a remote water source and the base 31 of humidifier chamber 8 at a water intake spout 21. The water source (not shown) may be, for example, a disposable bag or bottle which is positioned or hung relative to control housing 1, such that water is supplied to delivery tube 20 under the influence of gravity. Delivery tube 20 is interfaced with a solenoid operated, normally closed pinch valve 22 which is periodically opened to permit a measured volume of water (e.g. approximately 2 cc) to be controllably delivered by way of tube 20 and intake spout 21 to a humidifier chamber water reservoir (best shown in FIG. 2) at the interior of the base portion 31.

A control panel 23 is positioned at housing 1 to permit easy operation and observation by appropriate medical personnel. Control panel 23 includes a keyboard having four pressure activated touch pads 24 (designated SET TEMP), 25-1, 25-2, and 29 (designated RESET/RECALL). The touch pads permit adjustment of the predetermined temperature of the humidified air to be delivered to the patient. Control panel 23 also includes a digital temperature display 26 designated PROX TEMP) at which either the predetermined or actual temperature of the humidified air to be delivered to the patient can be selectively indicated. Also included at control panel 23 are four light emitting diode indicator lamps 28-1 (designated POWER), 28-2 (designated WATER), 28-3 (designated HI TEMP), and 28-4 (designated INOP). The indicator lamps provide a visual indication and/or warning regarding various humidifier system operating conditions. Details relating to the particular function and operation of control panel 23 and the aforementioned components thereof will be disclosed hereinafter when referring to FIG. 8 of the drawings.

The humidifier system housing 1 also includes a main on-off switch 2 by which to manually control the supply of electrical power from an AC source to the soon to be described control circuitry at housing 1. Moreover, housing 1 is also provided with an alarm 3 by which to provide audible warning signals in the event of the occurrence of certain undesirable system operating conditions, the nature of which will also soon be described.

Figure 2:
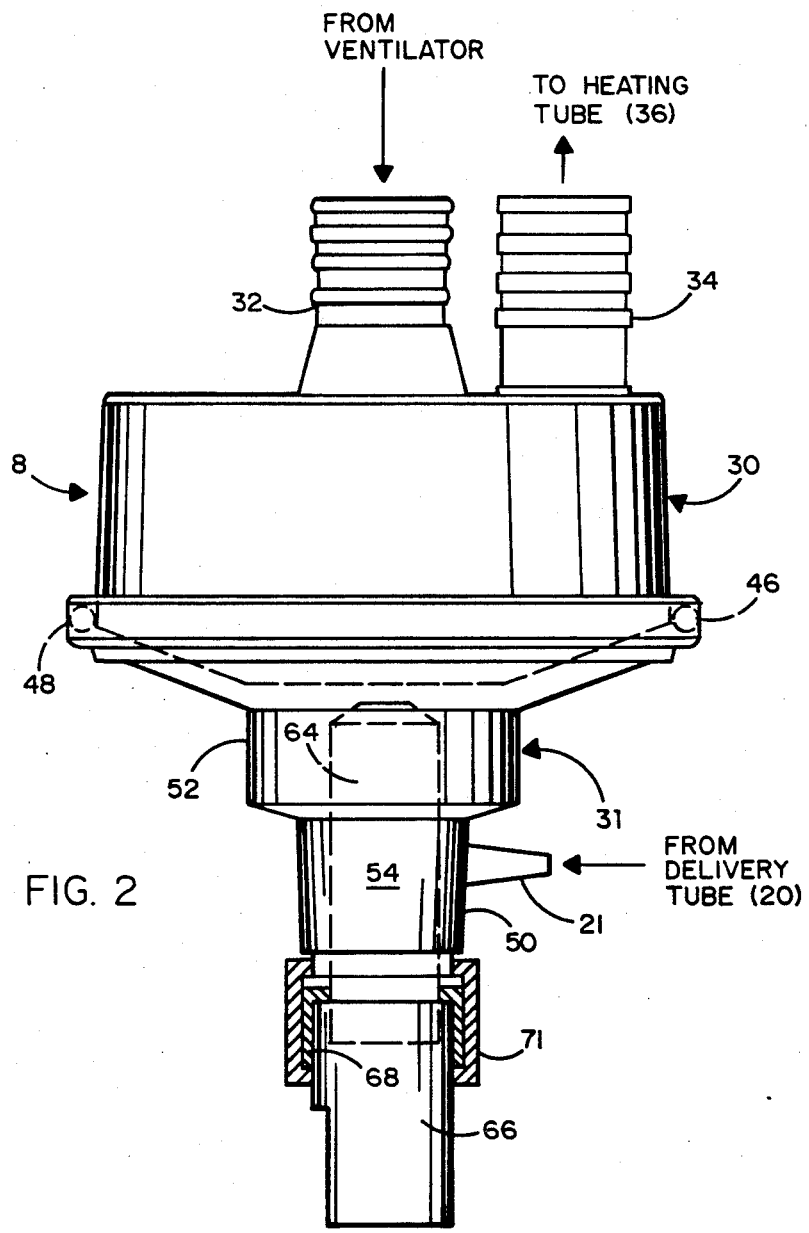
FIG. 2 is a front elevational view of the humidifier chamber of FIG. 1.
Figure 3:
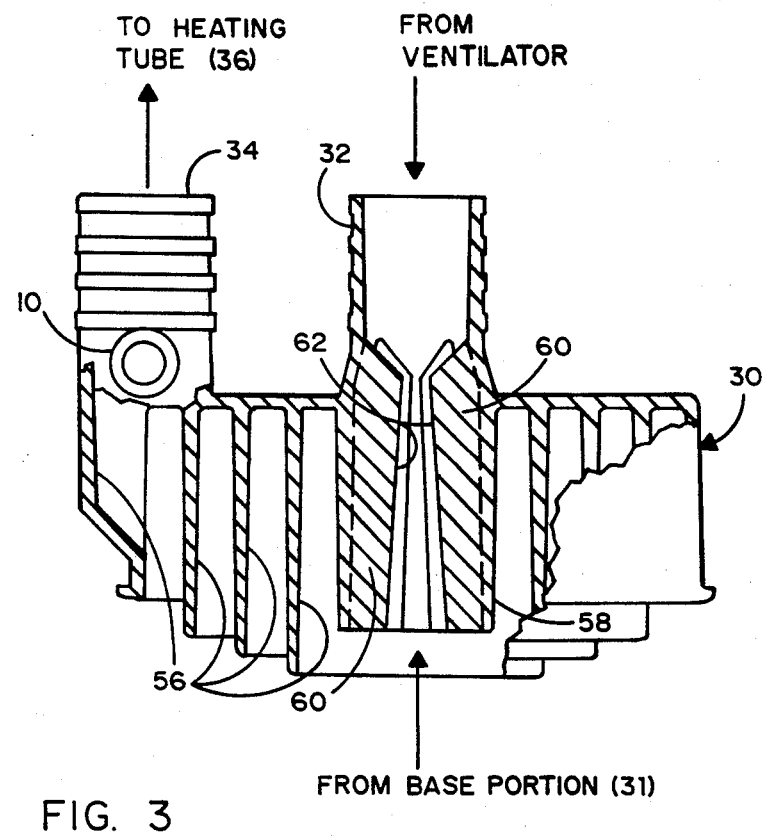
FIG. 3 is a cross-section of a shroud portion of the humidifier chamber of FIG. 1.
Figure 4:
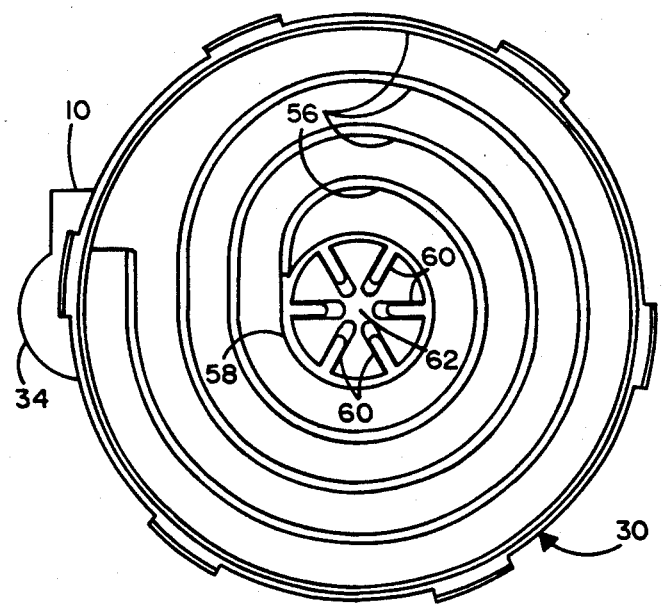
FIG. 4 is a bottom view of the shroud portion of the humidifier chamber of FIG. 1.

Humidifier chamber 8 is now described while referring to FIGS. 2-4 of the drawings. As previously disclosed while referring to FIG. 1, humidifier chamber 8 comprises a generally cylindrical shroud portion 30 (best illustrated in FIGS. 3 and 4) and a generally tapered base portion 31. Projecting upwardly from the top of shroud portion 30 are the air inlet and outlet ports 32 and 34. As previously indicated, air inlet port 32 is adapted to be interfaced with a ventilator, so as to receive a supply of incoming air therefrom. As also previously indicated, air outlet port 34 is adapted to be interfaced with heating tube 36 (of FIG. 1) for delivering humidified air to the patient. Base portion 31 includes an annular flange 46 or cover extending around the periphery at the top end thereof. Annular flange 46 has a diameter which is slightly larger than that of the shroud portion 30. Thus, the bottom of shroud portion 30 is of suitable dimension to be removably received and retained within the annular flange 46 of base portion 31. A sealing O-ring 48 may be disposed between the flange 46 and the bottom of shroud portion 30, so as to seal the shroud portion 30 within base portion 31.

Base portion 31 includes a hollow, cylindrical water reservoir 50 formed at the bottom end thereof. Projecting outwardly from reservoir 50 is the water intake spout 21 which is to be interfaced with a water delivery tube (designated 20 in FIG. 1), so that a small supply (e.g. 2 cc) of water can be provided from a source thereof to reservoir 50. Located between reservoir 50 and annular cover flange 46 is a hollow, cylindrical water return reservoir 52. The diameter of water return reservoir 52 is preferably larger than that of reservoir 50. Water reservoirs 50 and 52 communicate with one another for a purpose that will soon become apparent.

Extending through reservoirs 50 and 52 and projecting outwardly from the bottom end of base portion 31 is the main heater assembly 54 (the details of which will be described in greater detail when referring to FIGS. 5-7 of the drawings). Briefly, however, heater assembly 54 is comprised of a housing portion 64 and a connector portion 66. The housing and connector portions 64 and 66 are connected together by a retaining ring 68 which is surrounded by and coupled to a clamp 69 for the purpose of securing heater assembly 54 to the base portion 31 of humidifier chamber 8 (best shown in FIG. 5). Water delivered via intake spout 21 to reservoir 50 is heated and boiled therein by heater assembly 54. The steam generated as a result of such boiling water passes from reservoir 50 to the humidifier chamber heat exchange path which is located within shroud portion 30, the details of which are now described.

Referring concurrently to FIGS. 3 and 4 of the drawings, the humidifier chamber heat exchange path is shown extending through shroud portion 30 between the previously described air inlet and outlet ports 32 and 34. More particularly, and in accordance with the present invention, humidifier chamber portion 30 comprises a continuous heat exchange contact surface 56 which spirals outwardly from a distal end at a centrally disposed and cylindrically shaped vapor storage chamber 58 to a proximal end at air outlet port 34. The heat exchange spiral 56 is preferably fabricated from polysulfone (as is shroud portion 30) and provides a continuous contact surface of approximately 20 inches (51 cm) in the presently described embodiment. The vapor storage chamber 58 includes a plurality of fingers 60 which project radially inwardly. Fingers 60 terminate so as to form a gap 62 therebetween which extends axially throughout chamber 58. Vapor storage chamber 58 is coextensively formed and concentrically aligned with air inlet port 32, so that incoming air supplied by a ventilator is delivered to the vapor storage chamber 58 and the gap 62 formed between the fingers 60. The outermost or proximal end (relative to the centrally disposed vapor storage chamber 58) of the spiralling contact surface 56 of shroud portion 30 communicates with air outlet portion 34, whereby humidified air can be supplied at a predetermined temperature (e.g. 35° C.) to the patient by way of outlet port 34 and the heating tube (designated 36 in FIG. 1).

As previously indicated, temperature probes 10 and 12 are respectively interfaced with outlet port 34 and the patient wye 14 (of FIG. 1), so that the temperature of the humidified air being delivered to the patient via heating tube 36 can be sensed and controlled for the purpose of achieving a predetermined air temperature as set at the control panel (designated 23 in FIG. 1) of housing 1. The manner by which the temperature of the humidified air is sensed and controlled for providing the patient with air having the predetermined temperature will be described when referring to FIG. 9 of the drawings.

Figure 5:
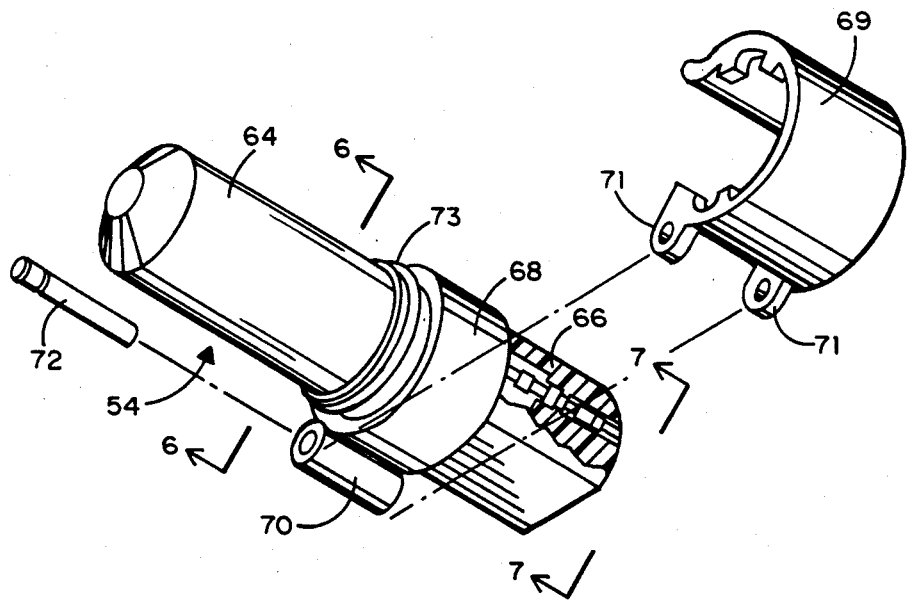
FIG. 5 is an isometric view of the main heating assembly which is disposed within the base portion of the humidifier chamber of FIG. 1.
Figure 6:
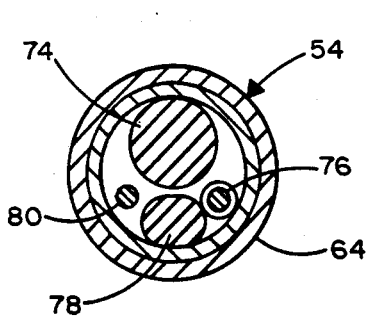
FIG. 6 is a cross-section of the main heater assembly taken along lines 6—6 of FIG. 5 to illustrate the relative alignment of the electrical components which are housed therein.
Figure 7:
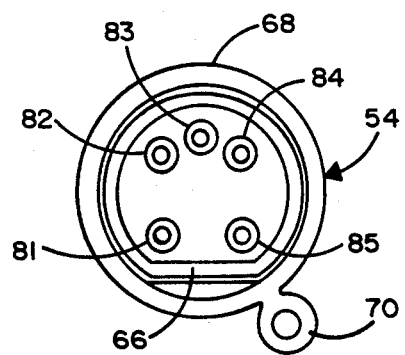
FIG. 7 is an end view of the main heater assembly taken along lines 7—7 of FIG. 5.

The details of the main heater assembly, designated 54 in FIG. 2, are now described while referring to FIGS. 5-7 of the drawings. As was previously indicated and as is best shown in FIG. 5, heater assembly 54 comprises a heater housing portion 64 and a connector portion 66. The heater housing portion 64 is preferably fabricated from aluminum which is anodized with a suitable impregnation coating. The connector portion 66 is preferably fabricated from plastic. The housing and connector portion 64 and 66 are adapted to be sandwiched together by a plastic retaining ring 68 which surrounds heater assembly 54 and is ultrasonically welded to connector portion 64. Retaining ring 68 is surrounded by and coupled to a clamp 69 at respective coextensively formed, cylindrical bosses 70 and 71. A locking and pivot pin 72 is inserted through an alignment of the bosses 70 and 71 of retaining ring 68 and clamp 69 to prevent a disengagement therebetween. As previously described when referring to FIG. 2, clamp 69 functions to secure the main heater assembly 54 within the base portion 31 of humidifier chamber 8. An O-ring 73 surrounds heater assembly 54 between the housing and connector portions 64 and 66 to form a more secure water-tight connection and prevent leakage from the reservoir water supply of humidifier chamber 8 when heater assembly 54 is extended therethrough.

As is best illustrated in FIG. 6, the housing portion 64 of main heater assembly 54 includes the spaced arrangement of a heating element 74, a water refill thermistor 76, a microfuse 78, and a ground terminal 80. The heating element 74 is preferably a conventional 200 watt resistance heater, such as that manufactured by Watlow Corporation. With main heater assembly 54 positioned in the assembled relationship at humidifier chamber 8 (of FIG. 2), heating element 74 is adapted to generate sufficient heat to quickly boil the relatively small supply contained by reservoir 50 of the humidifier chamber base portion 31. The water refill thermistor 76 is adapted to sense an increase in temperature (e.g. beyond 110° C.) corresponding to a depletion of the water supply at reservoir 50. Refill thermistor 76 thereby provides an indication that reservoir 50 must be refilled with additional water from the source thereof. Microfuse 78 has a temperature sensitive, chemical fuse link which is adapted to rupture at excessive (e.g. above 150° C.) heater assembly temperatures, whereby to de-energize the main heater element 74 and interrupt the supply of heat for boiling water in reservoir 50. An example of such a microfuse is Model No. 4300 manufactured by Micro Devices Corporation. As is apparent, microfuse 78 is included within the main heater assembly 54 to prevent damage to the humidifier chamber should heating element 74 overheat as a consequence of an undesirable operating condition during the utilization of the presently described humidifier system. Ground terminal 80 is electrically interconnected with the aluminum casing of the heater housing portion 64 of main heater assembly 54.

Extending through the connector portion 66 of main heater assembly 54 for electrical connection with the heating element 74, refill thermistor 76, microfuse 78, and ground terminal 80 are a plurality of five electrical connector pins 81-85 (best illustrated in FIG. 7) by which electrical power is supplied to assembly 54. More particularly, the heater assembly heating element 74 and the microfuse 78 are connected in electrical series between a first pair of connector pins 81 and 85, such that an open circuit caused by a rupture of the chemical fuse link of microfuse 78 in response to an overheating of element 74 will result in a termination of the current supply to heating element 74 and a discontinuation of the heating operation. Water refill thermistor 76 is electrically connected between a second pair of connector pins 82 and 84. Ground terminal 80 is electrically connected between the fifth connector pin 83 and the casing of the heater housing portion 64, as previously indicated.

The operation of and the cycling of air flow through the humidifier chamber 8 for supplying humidified air to a patient at a predetermined temperature (e.g. 35° C.) is now described while referring concurrently to FIGS. 2-7 of the drawings. During the start-up of the humidifier system, the reservoir 50 of humidifier chamber base portion 31 is initially devoid of water. Current is drawn by the heating element 74 of main heater assembly 54 so as to cause the temperature of heater assembly 54 to be raised beyond 110° C. This increased temperature is sensed by the water refill thermistor 76 of main heater assembly 54 so as to provide an indication that reservoir 50 must be filled with water from the remote source thereof. Accordingly, the solenoid operated pinch valve (designated 22 in FIG. 1) at housing 1 is opened for a time sufficient to permit an amount (e.g. 2 cc) of water to be provided to reservoir 50 from the source thereof by way of delivery tube 20 and water intake spout 21.

The relatively small water supply at reservoir 50 of base portion 31 is subsequently boiled by the main heater assembly 54, and the resulting steam is conveyed to the vapor storage chamber 58 of shroud portion 30. During that portion of the patient's breathing cycle referred to as exhalation, a supply of vapor is deposited in the vapor storage chamber 58 of the humidifier chamber shroud portion 30. The air at storage chamber 58 is over-heated and over-humidified (beyond the predetermined set points), so as to cause a thin layer of water to form around the surface of chamber 58. Excess water is drained, by means of gravity, from vapor storage 58 to the water return reservoir 52 (of FIG. 2) of base portion 31 where it may be reboiled and revaporized.

During that portion of the patient's breathing cycle referred to as inspiration (i.e. when incoming air is supplied to the air inlet port 32 of shroud portion 30 by a ventilator), air is pumped through the gap 62 of vapor storage chamber 58 where it acquires an excess of vapor. The vapor saturated air is then supplied to the distal end of the spiral heat exchange contact surface 56 of shroud portion 30. Hence, water will rain out (condense) from the vapor saturated air as it traverses the spiral path of the continuous and relatively cooler heat exchange surface 56 so as to assure 100 percent relative humidity. Such water is drained, by means of gravity, from the heat exchange surface 56 of shroud portion 30 to the water return reservoir 52 of base portion 31 to be reheated thereat. The temperature of the outgoing humidified air decreases around spiralling contact surface 56 until the temperature of the air at the proximal or patient end of contact surface 56 is approximately equal to the surface temperature of that portion of humidifier chamber 8 which communicates with air outlet port 34. That is, air which is initially characterized by high vapor density and temperature migrates through heat exchange surface 56 from vapor storage chamber 58 to air outlet port 34. During such migration and contact with heat exchange surface 56, the vapor density and temperature of the air decrease. Accordingly, the relative humidity and temperature of the outgoing air supplied from outlet port 34 to the heating tube 36 for delivery to the patient can be accurately controlled depending upon the length of the path established by spiralling contact surface 56 for achieving the preferred (100 percent) relatively humidity and (35° C.) temperature.

At the completion of the inspiration portion of the patient's breathing cycle, vapor may be exhausted from the vapor storage chamber 58, such that chamber 58 becomes dry. Nevertheless, there is normally sufficient vapor remaining within the heat exchange shroud portion 30 to fully humidify the entire breath of the patient. In the event that insufficient vapor remains in the shroud portion 30 after inspiration is completed, the end of the patient's breath will be characterized by relatively low temperature and humidity. However, the outgoing air can be conditioned during the patient's next breath to achieve the desired temperature (35° C.) and relative humidity (100 percent) in a manner and by means of the humidifier system control circuitry which is now disclosed in detail while referring concurrently to FIGS. 1 and 8 of the drawings.

Figure 8:
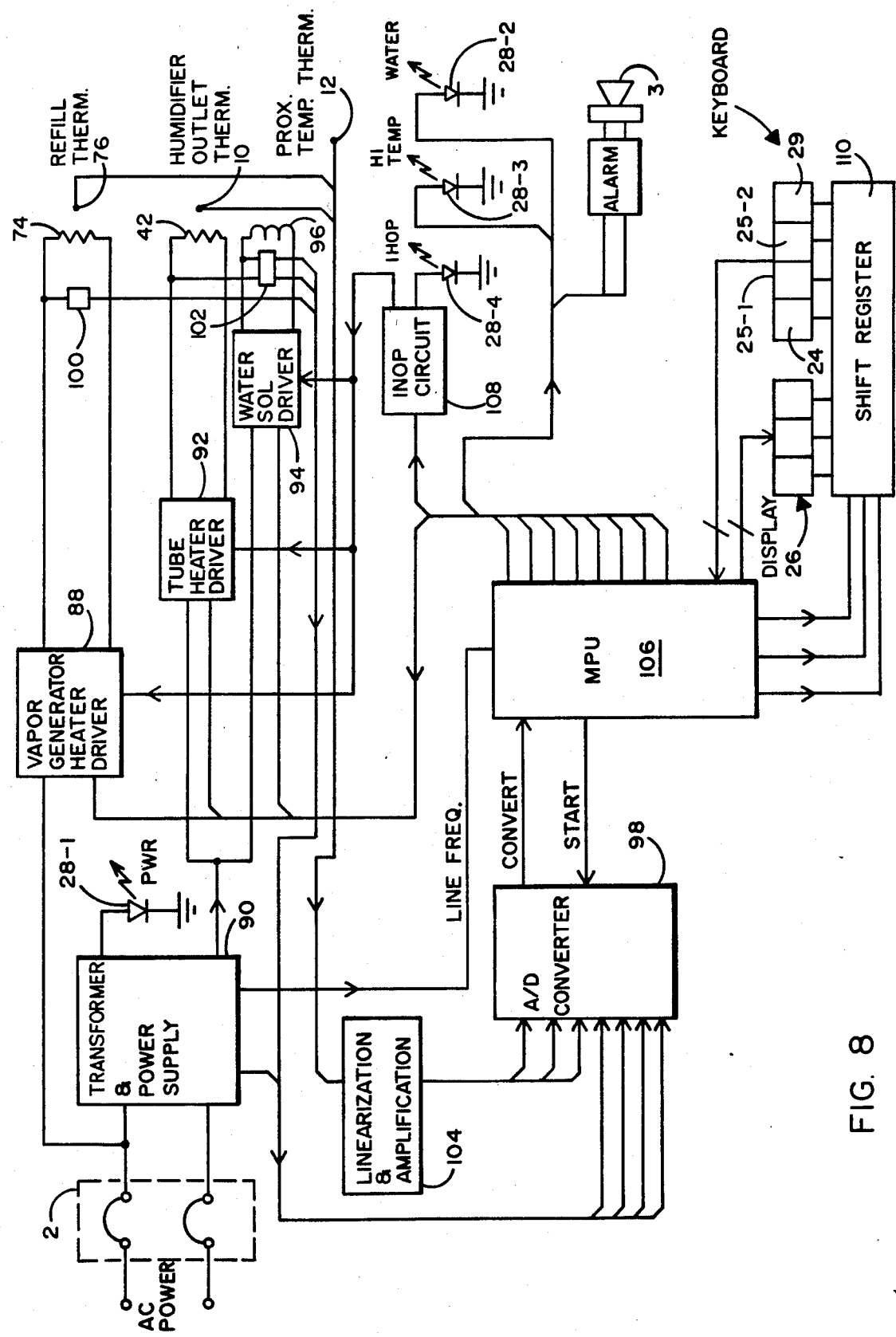
FIG. 8 is a block diagram which is representative of the control circuitry which also forms part of the presently disclosed humidifier system.

The microprocessor based control circuitry of FIG. 8 is preferably implemented on printed circuit boards which are located at the interior of humidifier system housing 1. As previously indicated, the control circuitry includes a control panel (designated 23 in FIG. 1) which is positioned at housing 1 to permit easy access to and inspection by attendant medical personnel. The control panel includes touch pads 24, 25-1, 25-2, and 29; digital display 26; and light emitting diode (LED) indicator lamps 28-1, 28-2, 28-3, and 28-4. The humidifier system software automatically presets the proximal air temperature (i.e. the temperature of the humidified air to be delivered to the patient from patient wye 14 at 35° C. In the event that the user wishes to change the proximal temperature from the aforementioned preset temperature, he depresses the SET TEMP touch pad 24 at the same time that he depresses either touch pad 25-1 (to increase the preset proximal temperature) or touch pad 25-2 (to lower the preset proximal temperature). The new, manually set proximal temperature will be displayed by digital display 26. When the SET TEMP touch pad 24 is released, display 26 indicates the actual proximal temperature, as sensed by the proximal temperature probe (i.e. thermistor) 12 at patient wye 14.

Whenever the main switch 2 of housing 1 is closed to permit power to be supplied to the humidifier system control circuitry, the (green) POWER indicator lamp 28-1 at control panel 23 is illuminated. When the reservoir of humidifier chamber 8 receives either an insufficient or excess supply of water, the (yellow) WATER indicator lamp 28-2 at control panel 23 is illuminated. At any time that the actual proximal temperature (sensed by proximal temperature thermistor 12) exceeds the predetermined temperature (either 35° C. or that manually set after depressing SET TEMP touch pad 24) by more than a particular amount (e.g. 2.5° C.). The (red) HI TEMP indicator lamp 28-3 at control panel 23 is illuminated. In the event that the proximal temperature sensed by thermistor 12 exceeds a particular temperature limit (e.g. 41° C.), the (red) INOP indicator lamp 28-4 at control panel 23 is illuminated.

In addition to the visible warning signals provided by indicator lamps 28-2, 28-3, and 28-4, an audible warning signal is simultaneously provided by the alarm (designated 3 in FIG. 1) during the occurrence of any of the previously-mentioned undesirable humidifier system operating conditions. The system software may also cause alarm 3 to be sounded in the event that either of the proximal temperature (sensed by thermistor 12) or the humidifier chamber outlet temperature (sensed by thermistor 10) drops below a predetermined temperature limit (e.g. 7° C.); the temperature of the main heater assembly 54 (sensed by thermistor 76) exceeds or drops below a predetermined temperature limit (e.g. 150° C. and 7° C., respectively), or the system fails to complete a software-controlled self-test routine.

The activation of indicator lamps 28-2, 28-3, and 28-4 and/or alarm 3 indicates the need for manual intervention, inspection, and possible correction of the undesirable operating condition. The indicator lamps 28-2, 28-3, and 28-4 and/or the alarm 3 will remain energized until the undesirable condition is remedied and the user depresses the RESET/RECALL touch pad 29 at the keyboard of control panel 23.

The on/off switch 2 at housing 1 is electrically connected between an available source of AC power and each of a vapor generator heater driver 88 and a step-down transformer 90. Thus, when switch 2 is closed, AC power is supplied to both driver 88 and transformer 90. Vapor generator heater driver 88 preferably comprises a pair of MCR72-6 silicon controlled rectifiers, such as that manufactured by Motorola Corporation, which are electrically interconnected in series (for redundancy) with the heating element 74 of the main heater assembly (54 in FIG. 5). Heater driver 88 supplies current to heating element 74, so that the reservoir water supply can be boiled and vapor subsequently generated within humidifier chamber 8.

The transformer 90 is preferably characterized by a primary winding having a 120/240 volt capacity and a secondary winding having a 24 volt center tap connection. AC output voltage from the secondary winding of transformer 90 is supplied to power each of a tube heater driver 92 and a water solenoid driver 94. The tube heater driver 92 preferably comprises an MCR72-6 silicon controlled rectifier, such as that manufactured by Motorola Corporation, which is electrically interconnected with the heater element 42 of the heating tube (36 of FIG. 1) in the event that optional heater element 42 is to be utilized. Tube heater driver 92 controls the supply of current to heater element 42 so that the heat generated thereby is adapted to avoid condensation and reduce temperature fluctuations of humidified air within the heating tube 36 (of FIG. 1).

The water solenoid driver 94 preferably comprises a TIP120 Darlington transistor, such as that manufactured by Motorola Corporation, which is electrically interconnected with a solenoid 96. Solenoid 96 is interfaced with solenoid controlled pinch valve 22 at housing 1. As earlier indicated, pinch valve 22 is periodically opened for a time sufficient to permit a controlled amount (e.g. 2 cc) of water to be added to the reservoir of humidifier chamber 8 via delivery tube 22 and water intake spout 21. In the event that the reservoir water supply becomes depleted, the temperature sensed by refill thermistor 76 will begin to rise. When the reservoir temperature exceeds a predetermined temperature limit (e.g. 110° C.), the water solenoid driver 94 is activated. Accordingly, water solenoid driver 94 energizes solenoid 96 to cause pinch valve 22 to be opened and the humidifier chamber reservoir to be replenished (by means of gravity) from a water source. Should the reservoir fail to receive an additional supply of water (e.g. because the source is empty), the reservoir temperature will continue to rise to 130° C. at which temperature the aforementioned LED indicator lamp 28-2 at the control panel 23 of housing 1 is illuminated, so as to provide a visual warning of the depleted reservoir water supply.

The output voltage from transformer 90 is also rectified, such as by means of a full wave rectifier (not shown), for supplying DC power (e.g. 12 volts DC) for driving alarm 3, digital display 26, and LED indicator lamps 28-1, 28-2, 28-3, and 28-4. A rectified DC voltage (e.g. 0-2 volts) is also supplied from transformer 90 to an input terminal of an analog to digital converter 98 to provide converter 98 with a source of reference potential. More particularly, analog to digital converter 98 is preferably a single slope converter, such as a 14443 microelectronic chip manufactured by Motorola Corporation. That is, analog to digital converter 98 is adapted to provide an output pulse, the width of which is proportional to the voltage level of a selected one of a plurality (e.g. six) of input signals. Three input signals are respectively applied to corresponding input terminals of analog to digital converter 98 from a pair of opto-isolators 100 and 102. Opto-isolator 100 is electrically interfaced with the heating element 74 (of heater assembly 54), and opto-isolator 102 is electrically interfaced with each of the heater element 42 (of heating tube 36) and solenoid 96. Each of opto-isolators 100 and 102 is preferably an H11G2 microelectronic chip, such as that manufactured by Motorola Corporation, which includes a light emitting diode optically coupled to a semiconductor switching device. Opto-isolators 100 and 102 are adapted to monitor the state of (i.e. sense current drawn by) resistance elements 74 and 42 and inductance element 96. That is, when sufficient current is drawn by heating element 74 or either of heater element 42 or solenoid 96 to energize a respective opto-isolator light emitting diode, the corresponding optically coupled switch is rendered conducting, and a corresponding input signal is supplied from opto-isolator 100 and/or 102 to analog to digital converter 98 to indicate the energization of elements 74 and/or 42 or 96.

Three additional input signals are applied to corresponding input terminals of analog to digital converter 98 from thermistors 10, 12, and 76, respectively, by way of a conventional linearization and amplification circuit 104. In order that suitable information may be supplied to a microprocessor unit 106, linearization and amplification circuit 104 linearizes and amplifies, via respective CA3260AE high again amplifiers (such as that manufactured by RCA Corporation), the three non-linear signals which are indicative of the temperature of the humidified air at the outlet port 34 of humidifier chamber 8 (sensed by thermistor 10), the proximal temperature of the humidified air being delivered to the patient from heating tube 36 (sensed by thermistor 12), and the temperature of main heater assembly heating element 74 (sensed by thermistor 76).

The control circuit microprocessor unit 106 is electrically interconnected with analog to digital converter 98 so as to enable converter 98 (via an output line designated START) and to receive information (via an input line designated CONVERT) from which the proximal temperature of the humidified air being delivered to the patient can be sensed and subsequently adjusted in accordance with the system software (the nature of which will be explained when referring to FIG. 9 of the drawings). Microprocessor unit 106 is preferably a 146805E2 microelectronic chip which is interfaced with an auxilary 2732 EPROM microelectronic chip (both chips being readily available commercially to provide memory for storing the system software. Microprocessor unit 106 is also connected to transformer 90 so as to receive a signal (via an input line designated LINE FREQ) which is indicative of the frequency (e.g. zero crossings) of the rectified DC voltage provided thereby, so that the AC line voltage and the DC rectified voltage can be monitored to assure the presence of suitable operating voltage levels. Output signals from microprocessor unit 106 are provided to control the operations of the alarm 3, display 26, and LED indicator lamps 28-2 and 28-3, vapor generator driver 88, tube heater driver 92, water solenoid driver 94, and an INOP circuit 108.

Electrically connected to respective input terminals of each of vapor generator heater driver 88, tube heater driver 92, and water solenoid driver 94, is a microprocessor controlled circuit 108 (designated INOP). The INOP circuit 108 is preferably a 7555 microelectronic chip, such as that manufactured by GE Intersil Corporation, utilized as a one-shot multivibrator. In the event that an undesirable operating condition is detected by microprocessor unit 106, the INOP circuit 108 is activated to deenergize vapor generator heater driver 88, tube heater driver 92, and water solenoid driver 94 to prevent the additional delivery of water and the continued heating thereof at the reservoir of humidifier chamber 8 so as to avoid the possibility of damage to chamber 8 until the undesirable operating condition has been remedied. That is, the INOP multivibrator circuit 108 is retriggered in response to a train of input pulses supplied from microprocessor unit 106 during the occurrence of conditions which are indicative of normal humidifier system operation. Thus, the output of INOP circuit 108 in response to the pulse train is a relatively HI logic level signal. When an undesirable operating condition is detected microprocessor unit 106 (e.g. such as an excessive proximal temperature sensed by proximal temperature thermistor 12), the output pulse train supplied from microprocessor unit 106 to INOP circuit 108 is terminated, so that the INOP multivibrator is no longer retriggered. Hence, the INOP multivibrator will time out, and will put out a relatively LOW logic level signal, to deenergize drivers 88, 92, and 94 and prevent further humidifier system operation until a correction is made. At the same time, the aforementioned LED indicator lamp 28-4 at the control panel 23 of housing 1 is illuminated (and alarm 3 may also be sounded), so as to provide to attendant medical personnel a visual warning of the occurrence of such an undesirable operating condition.

Microprocessor unit 106 is interfaced with display 26 (as already indicated) and a shift register 110, so that information can be displayed regarding the predetermined air temperature and the actual proximal temperature of the humidified air being supplied to the patient (as sensed by thermistor 12). Shift register 110 is preferably a 74HC164 microelectronic chip, such as that manufactured by Motorola Corporation, which is adapted to scan the keyboard (comprising touch pads 24, 25-1, 25-2, and 29), so as to determine the entry of any change in the present proximal temperature, whereby either of the preset temperature (i.e. 35° C.) or the new, manually set temperature can be indicated at display 26.

Figure 9:
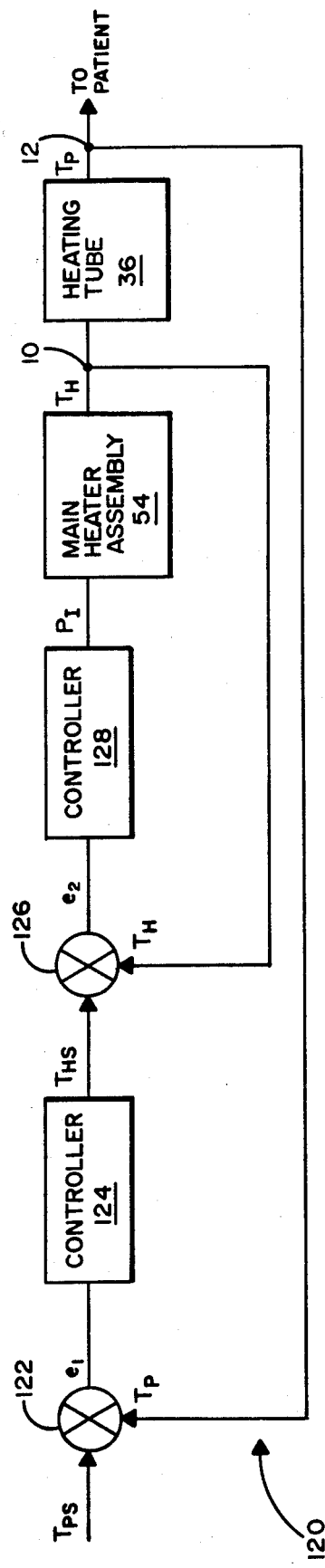
FIG. 9 is a schematic of a closed loop, servo-controlled system of the present invention for controlling the temperature of the humidified air that is supplied from the humidifier to the patient.

Referring now to FIG. 9 of the drawings, a closed loop, dual servo controller 120 is depicted by which the humidifier system software controls the operation of the main heater assembly 54 (best illustrated in FIG. 5), so that the proximal temperature of the humidified air being delivered to a patient can be adjusted and maintained at a predetermined temperature. More particularly, servo controller 120 includes a first comparator 122 which receives a pair of input signals. A first input signal (designated $T_{PS}$) supplied to comparator 122 is indicative of either the temperature (i.e. 35° C.) as preset by the system software or a newly set temperature as entered manually at the keyboard of control panel 26 (of FIG. 1). The second input signal (designated $T_P$) supplied to comparator 122 is indicative of the actual proximal temperature of the humidified air (as sensed by proximal temperature thermistor 12.

The output of comparator 122 is an error signal (designated $e_1$) which is indicative of the difference between the magnitudes of the input signals $T_{PS}$ and $T_P$. This error signal $e_1$ is applied to a floating controller 124. Controller 124 is adapted to convert the error signal $e_1$ from comparator 122 into a temperature signal which is proportional to such error. Depending upon the error input signal $e_1$, the output signal (designated $T_{HS}$) from controller 124 is a software determined temperature which represents an estimate of a set point temperature to which the humidified air must be heated at the outlet port 34 of humidifier chamber 8 (of FIG. 1) in order to ultimately achieve the desired proximal temperature $T_P$. This estimated, software established set point temperature $T_{HS}$ at output port 34 may be represented as follows:

$$T_{HS} = T_{PS} + K_1 e_1 + 1/K_2 \int e_1 dt;$$

where
$e_1 = T_{PS} - T_P$, and
$K_1$ and $K_2$ are constants.

The output signal $T_{HS}$ from controller 124 is supplied to a first input terminal of a second comparator 126. Supplied to a second input terminal of comparator 126 is a signal (designated $T_H$) which is indicative of the actual temperature of the humidified air at the outlet port 34 of humidifier chamber 8 (as sensed by thermistor 10). The output of comparator 126 is another error signal (designated $e_2$) which is indicative of the difference between the magnitudes of the input temperatures $T_{HS}$ and $T_H$. This error signal $e_2$ is supplied to another controller 128. Controller 128 is adapted to control the input power to main heater assembly 54 by providing an input signal (designated $P_I$) to vapor generator heater driver 88 (of FIG. 8), which signal is proportional to the magnitude of the error signal $e_2$ developed by comparator 126. More particularly, the signal $P_I$ supplied by controller 128 to heater driver 88 acts to regulate the power level or duty cycle of the main heater assembly 54, so that sufficient heat is generated thereby to minimize the error signal $e_2$. This input signal $P_I$ which is applied to the vapor generator heater driver to regulate the duty cycle and power level of heater assembly 54 may be represented as follows:

$$P_I = K_3 e_2 + 1/K_4 \int e_2 dt + K_5 de_2/dt;$$

where
$e_2 = T_{HS} - T_H$, and
$K_3$, $K_4$ and $K_5$ are constants.

The temperature of the humidified air, which is heated by the main heater assembly 54, is sensed by thermistor 10 at the air outlet port 34 of humidifier chamber 8 and, as previously disclosed, a signal $T_H$, which is representative of this temperature, is fed back via a first feedback path to an input terminal of comparator 126. The temperature of the humidified air which is heated by heating tube 36 and delivered to the patient is sensed by thermistor 12 at the patient wye 14 (of FIG. 1) and, as previously disclosed, a signal $T_P$, which is representative of this temperature, is fed back via a second feedback path to an input terminal of comparator 122. By monitoring the air temperature at both outlet port 34 and patient wye 14, fluctuations in the temperature of the air delivered to the patient can be minimized.

The power level or duty cycle of the tube heater driver 92 (of FIG. 8) is controlled by a software generated signal (designated $P_{THDR}$), which signal may be represented as follows:

$$P_{THDR} = K_6 P_I + K_7 (T_H - T_P);$$

where $K_6$ and $K_7$ are constants.

Accordingly, a relatively large temperature drop $(T_H - T_P)$ across heating tube 36 typically signifies excess moisture therein, whereby power to the tube heater driver is increased to eliminate condensation from tube 36. A relatively small temperature drop across heating tube 36 typically signifies little condensation within the tube and an outlet air temperature having 100 percent relative humidity. Therefore, power to the tube heater driver is reduced to avoid drying of and possible damage to the tube 36.

Hence, the presently disclosed humidifier system eliminates the shortcomings which are characteristic of conventional humidifier systems. That is, the present humidifier system has a relatively low cost, compact configuration which utilizes a permanent, reusable wick and a relatively small reservoir supply of water which can be rapidly heated to operating temperature. The system housing includes a control panel which is convenient to operate and provides easily read indications of system performance. In addition, the control circuitry provides a dual servo controller having two feedback paths to permit accurate monitoring and control of the proximal temperature of the patient air relative to a predetermined temperature, while maintaining substantially 100 percent relative humidity over a range of suitable air temperatures.

It will be apparent that while a preferred embodiment of the invention has been shown and described, various modifications and changes may be made without departing from the true spirit and scope of the invention. By way of example, the presently described humidifier system is applicable to infant as well as adult patients. However, for an infant application, it has been found that a higher humidifier chamber outlet temperature (designated $T_H$) is needed for any corresponding proximal air temperature (designated $T_P$). Accordingly, there is a greater tendency for condensation to develop along the heating tube 36 which necessitates the use of air heating tube 36 having a heater element 42 whereby to avoid such condensation.

Having thus set forth a preferred embodiment of the present invention, what is claimed is:

1. A humidifier system for heating and humidifying breathable gas supplied to a patient by a medical ventilator or other source of such gas, said system comprising:
   a chamber having a gas inlet adapted to receive breathable gas from a source thereof, a gas outlet for delivering the gas to the patient, and a reservoir;
   water intake means for periodically supplying a relatively small amount of water to said reservoir from a source thereof;
   water heater means, associated with said reservoir, for boiling the water in said reservoir to generate steam;
   vapor storage means in said chamber and communicating with said gas inlet and with said reservoir, for introducing the incoming gas from said inlet to the steam generated by said heater means, thereby heating said gas and saturating said gas with water vapor from said steam; and
   heat exchanger means, disposed between said vapor storage means and said gas outlet, for condensing vapor from the heated, vapor-saturated gas flowing from said vapor storage means, whereby heated gas at approximately 100 percent relative humidity is provided to said gas outlet for delivery to the patient.

2. The humidifier system recited in claim 1 wherein said reservoir and said vapor storage means are concentrically aligned with one another in said chamber.

3. The humidifier system recited in claim 1, wherein said vapor storage means is axially aligned with, and radially displaced from, said gas outlet in said chamber, said heat exchanger means including a continuous surface which spirals outwardly from said vapor storage means to said gas outlet.

4. The humidifier system recied in claim 1, wherein said water heater means includes a heat producing element connected in electrical series with a temperature responsive fuse link, such that a certain excessive water heater means temperature will cause said temperature responsive fuse link to rupture and thereby terminate the production of heat by said heat producing element.

5. The humidifier system recited in claim 1, wherein said water heater means includes a sensor which is responsive to the temperature of said water heater means, such that said sensor is adapted to provide a signal in response to a certain water heater means temperature for causing an additional supply of water to be added from the source thereof to said reservoir by said water intake means.

6. The humidifier system recited in claim 5, wherein said water intake means includes normally closed valve means for controlling the supply of water from the source thereof to the reservoir of said chamber, the signal provided by the temperature responsive sensor of said water heater means causing said valve means to open for a time sufficient to permit an additional supply of water to be added to said reservoir.

7. The humidifier system recited in claim 6, further including a solenoid for actuating said normally closed valve means and thereby controlling the supply of water to said reservoir, said signal provided by the temperature responsive sensor of said water heater means causing the energization of said solenoid and the opening of said valve means.

8. The humidifier system recited in claim 1, further including a gas heating tube communicating at a first end thereof with said gas outlet and at second and opposite end thereof with means adapted to be fluidly coupled to the respiratory system of a patient for delivering heated and humidified outgoing gas from said chamber to the patient, said tube having a heat producing element located therein by which to generate heat and thereby substantially prevent condensation within said tube.

9. The humidifier system recited in claim 8, further including a first temperature sensor interfaced with the first end of said gas heating tube and responsive to the temperature of the outgoing gas at said gas outlet; and
   a second temperature sensor interfaced with the second end of said tube and responsive to the temperature of the outgoing gas being delivered to the patient,
   the energization of said heat producing element and the generation of heat in said tube being dependent upon the difference between the respective temperatures to which said first and second sensors are responsive.

10. The humidifier system recited in claim 9, further including tube driver means for energizing the heat producing element in said gas heating tube, the output power provided by said tube driver means for energizing said heat producing element being dependent upon the difference between the respective temperatures to which said first and second temperature sensors are responsive.

11. The humidifier system recited in claim 9, further including water heater driver means for energizing said water heater means, the output power provided by said water heater driver means for energizing said water heater means being dependent upon the difference between the temperature to which the second temperature sensor is responsive and a predetermined temperature, so as to cause said water heater means to generate steam to heat the gas entering said vapor storage means until the predetermined temperature is substantially achieved by the gas flowing through said gas heating tube proximate said second temperature sensor.

12. The humidifier system recited in claim 8, further including circuit means interconnected with each of a tube driver means for energizing the heat producing element of said gas heating tube and a water heater driver means for energizing said water heater means, said circuit means being responsive to the temperatures to which said heat producing element and said water heater means are heated so as to deenergize said heat producing element and said water heater means in the event that a temperature to which said circuit means is responsive exceeds a predetermined temperature level.

13. A humidifier system, comprising:

a chamber having a gas inlet for receiving breathable gas from a source thereof, a gas outlet, and a water reservoir;

water intake means for periodically supplying a relatively small amount of water to said reservoir from a water source;

a tube having a first end connected to said gas outlet, a second end adapted to be coupled to the respiratory system of a patient, and a heating element disposed between said first and second ends;

water heater means in said chamber, and operably associated with said reservoir, for boiling the water in said reservoir, thereby generating steam which heats and vapor-saturates the gas flowing into said chamber through said gas inlet;

heat exchanger means in said chamber for (a) receiving the heated, vapor-saturated air, and (b) cooling the vapor-saturated gas to cause the condensation of vapor therefrom as said gas travels to said outlet, whereby the gas at said outlet has a relative humidity of approximately 100 percent and a lower temperature than when said gas is received by said heat exchanger means;

first temperature-sensing means for sensing the gas temperature at or near the second end of said tube;

second temperature-sensing means for sensing the gas temperature at or near said gas outlet; and servo control means for controlling the heat generated by said heating element and said water heater means in response to the temperatures sensed by said first and second temperature-sensing means.

14. The humidifier system recited in claim 13, wherein said servo control means includes first comparator means and feedback path means by which the temperature at or near the second end of said tube is compared with predetermined temperature, said first comparator means providing an output signal which is indicative of the difference between the temperature at or near the second end of said tube and said predetermined temperature, said output signal controlling the energization of said water heater means to generate steam for heating the gas received by said heat exchanger means until the predetermined temperature is substantially achieved by the gas flowing through said tube proximate said first temperature-sensing means.

15. The humidifier system recited in claim 14, wherein said servo control means includes second comparator means and feedback path means by which the temperature at or near said gas outlet is compared with the output signal from said first comparator means, said second comparator means providing an output signal which is indicative of a comparison between the temperature at or near said gas outlet and said first comparator means output signal, said second comparator means output signal also controlling the energization of said water heater means to generate steam for heating the gas received by said heat exchanger means until the predetermined temperature is substantially achieved by the gas flowing through said tube proximate said first temperature-sensing means.

16. The humidifier system recited in claim 15, further comprising driver means for energizing the heating element of said tube and said water heater means, the output signals from said first and second comparator means regulating the output power provided by said driver means for controlling the energization of and heat generated by said heating element and said water heater means.

17. The humidifier system recited in claim 13, further comprising monitoring circuitry interconnected with each of said water heater means and the heating element of said tube, said monitoring circuitry monitoring the temperatures to which said first and second temperature sensors are responsive and adapted to disable said water heater means and said heating element should either of said temperatures or the difference therebetween exceed a predetermined limit.

18. The humidifier system recited in claim 13, wherein said chamber includes vapor storage means for introddcing the steam produced by said water heater means to the gas flowing into said chamber from said gas inlet, so that a substantially continuous supply of vapor saturated gas is available from said vapor storage means.

19. The humidifier system recited in claim 18, wherein said heat exchanger means includes a continuous surface which spirals outwardly from said vapor storage means to said gas outlet, so that heated gas having substantially 100 percent relative humidity can be delivered to the patient by way of said tube.

20. The humidifier system of claim 13, wherein said water intake means comprises solenoid operated valving means for controlling the supply of water from said water source to said reservoir.

21. A humidifer system for heating and humidifying breathable gas supplied to a patient by a medical ventilator, said system comprising:

a chamber having a gas inlet adapted to be coupled to said ventilator, a gas outlet, and a water reservoir;

water intake means for periodically supplying a relatively small amount of water to said reservoir from a water source;

steam-generating means, operatively associated with said reservoir, for (a) boiling the water in said reservoir to produce steam, and (b) introducing the air flowing through said gas inlet to said steam, thereby heating and vapor-saturating said gas;

heat exchanger means in said chamber configured to form a gas flow path between said steam-generating means and said gas outlet, for condensing water vapor from the heated, vapor-saturated gas received from said steam-generating means, whereby the gas at said outlet has a relative humidity of approximately 100 percent at a lower temperature than when said gas is recieved by said heat exchanger means;

a gas delivery tube having a first end coupled to said gas outlet and a second end adapted to be coupled to said patient;

temperature-sensing means for providing a temperature-indicative signal in response to the gas temperature at or near the second end of said gas delivery tube; and servo control means for controlling the energization of said steam-generating means in response to the value of said temperature-indicative signal.

22. The humidifer system recited in claim 21, wherein said servo control means comprises: comparator means, responsive to said temperature-indicative signal, for producing an output signal having a value indicative of the difference between the value of said temperature-indicative signal and a predetermined temperature value; and feedback means, responsive to said output signal, for applying said output signal to said steam generating means, whereby said steam-generating means is controlled so as to minimize the difference between the value of said temperature-indicative signal and said predetermined temperature value.

23. The humidifier system of claim 21, wherein said temperature-sensing means is a first temperature-sensing means providing a first temperature-indicative signal, wherein said system further comprises second temperature-sensing means for providing a second temperature-indicative signal in response to the gas temperature at or near said gas outlet, and wherein said servo control means comprises:

first comparator means, responsive to said first temperature-indicative signal, for producing a first output signal having a value indicative of the difference between the value of said first temperature-indicative signal and a predetermined temperature value;

second comparator means, responsive to said second temperature-indicative signal and to said first output signal, for producing a second output signal having a value indicative of the difference between the value of said second temperature-indicative signal and the value of said first output signal; and feedback means, responsive to said first and second output signals, for applying said first and second output signals to said steam-generating means so as to control the energization of said steam-generating means to minimize the difference between the value of said first temperature-indicative signal and said predetermined temperature value.

* * * * *